(12) United States Patent
Keal

(10) Patent No.: US 9,921,335 B1
(45) Date of Patent: Mar. 20, 2018

(54) SYSTEMS AND METHODS FOR DETERMINING LINEAR ACCELERATION

(71) Applicant: INVENSENSE INCORPORATED, San Jose, CA (US)

(72) Inventor: William Kerry Keal, Santa Clara, CA (US)

(73) Assignee: InvenSense, Inc., San Jose, CA (US)

( * ) Notice: Subject to any disclaimer, the term of this patent is extended or adjusted under 35 U.S.C. 154(b) by 345 days.

(21) Appl. No.: 14/680,993

(22) Filed: Apr. 7, 2015

(51) Int. Cl.
*G01V 7/00* (2006.01)
*G01V 7/02* (2006.01)

(52) U.S. Cl.
CPC ........................................ *G01V 7/02* (2013.01)

(58) Field of Classification Search
CPC ........ G01P 15/18; G01C 19/5776; G01V 7/02
USPC .................. 73/382, 382 G; 702/141, 150
See application file for complete search history.

(56) References Cited

U.S. PATENT DOCUMENTS

| | | | | |
|---|---|---|---|---|
| 2009/0322679 | A1* | 12/2009 | Sato et al. | A63F 13/02 345/158 |
| 2010/0214216 | A1* | 8/2010 | Nasiri et al. | A63F 13/06 345/158 |
| 2013/0106697 | A1* | 5/2013 | Kulik | G01C 17/38 345/158 |

* cited by examiner

*Primary Examiner* — Lisa Caputo
*Assistant Examiner* — Roger Hernandez-Prewitt
(74) *Attorney, Agent, or Firm* — Bay Area Technology Law Group PC

(57) ABSTRACT

Systems and methods are disclosed for deriving linear acceleration using an accelerometer. The orientation of a device may be determined using only accelerometer data. The determined orientation may then be used to determine a gravity vector, such that linear acceleration may be derived by subtracting the gravity vector from accelerometer data.

22 Claims, 4 Drawing Sheets

SYSTEMS AND METHODS FOR DETERMINING LINEAR ACCELERATION

FIELD OF THE PRESENT DISCLOSURE

This disclosure generally relates to techniques for processing data from an accelerometer sensor and more specifically to measuring linear acceleration using only accelerometer data.

BACKGROUND

The development of microelectromechanical systems (MEMS) has enabled the incorporation of a wide variety of sensors into mobile devices, such as cell phones, laptops, tablets, gaming devices and other portable, electronic devices. Non-limiting examples of sensors include motion or environmental sensors, such as an accelerometer, a gyroscope, a magnetometer, a pressure sensor, a microphone, a proximity sensor, an ambient light sensor, an infrared sensor, and the like. As the availability of sensors has increased, so too have the applications that utilize sensor data. For example, gesture recognition or orientation detection of a device equipped with sensors allows a user to input commands or data by moving the device or by positioning the device in a predetermined orientation. Any numbers of implementations exist, including allowing a user to select particular device functions by simply moving, shaking, or tapping the device. Such functionality can include motion gesture recognition implemented on motion sensing devices to allow a user to input commands or data by moving the device or otherwise cause the device to sense the user's motion. In light of this increased reliance on sensor information, the ability to provide relevant sensor data may be an important characteristic.

In many situations, operations known as sensor fusion may involve combining data obtained from multiple sensors to improve accuracy and usefulness of the sensor data, such as by refining orientation information or characterizing a bias that may be present in a given sensor. Although sensor fusion operations may provide enhanced data, the requirement of powering multiple sensor systems simultaneously may represent a significant expenditure of resources, both in terms of power consumption and computational demands. Particularly for mobile devices that may rely on a battery for energy or may have reduced computational abilities, the use of sensor fusion involving multiple sensor systems may represent an undesirably large portion of the resource budget. This is especially true for devices that have a small battery and where the specifications require a long battery life, so the user does not have the charge, or even replace, the battery very often. An example of such a device may be an portable activity monitoring device in the form of a bracelet or a (belt) clip. Accordingly, the techniques of this disclosure are directed to measuring linear acceleration using data from an accelerometer alone.

SUMMARY

As will be described in detail below, this disclosure includes a method for measuring linear acceleration using a device having an accelerometer. In one aspect, the method may involve obtaining a plurality of data samples from the accelerometer, iteratively determining a plurality of orientations of the device with respect to gravity using only sampled data from the accelerometer, determining a gravity vector with respect to a first data sample of the plurality of data samples using a determined orientation corresponding to the first data sample and subtracting the determined gravity vector from the first sample of data from the accelerometer to derive linear acceleration.

In an embodiment, a gain factor may be used to convert accelerometer data to an angle or an angular rate. The gain factor is based on a magnitude of accelerometer. Further, the gain factor may be adjusted dynamically. As desired, the gain factor may be obtained from a look up table.

In one aspect, each orientation may be determined as the sum of previous orientation and a correction rotation comprising terms orthogonal to gravity applied to a previous orientation. In an embodiment, an orientation of the device corresponding to sample N of the plurality of samples may be represented by $\overline{Q_N}$ and may be determined as:

$$\overline{Q_N} = \overline{Q_{N-1}} + \begin{bmatrix} 0 \\ A_{wy} * \text{gain} \\ -A_{wx} * \text{gain} \\ 0 \end{bmatrix} \otimes \overline{Q_{N-1}},$$

wherein $A_{wy}$ is acceleration on a y-axis in a world frame, $A_{wx}$ is acceleration on an x-axis in the world frame and gain is a factor selected to convert accelerometer data to an angle or an angular rate.

In another aspect, the gravity vector with respect to the first data sample may be determined by converting a gravity vector in a world frame to a body frame of the device using the determined orientation corresponding to the first data sample.

In an embodiment, the derived linear acceleration may be high pass filtered.

In an embodiment, determining the gravity vector may also include performing a sensor fusion operation with data from a magnetometer of the device.

In an embodiment, determining the gravity vector may also include performing a sensor fusion operation with a previously derived linear acceleration.

This disclosure also includes a device for measuring linear acceleration, wherein the device may have an accelerometer outputting a plurality of data samples, an orientation module configured to iteratively determine a plurality of orientations of the device with respect to gravity using only sampled data from the accelerometer and to determine a gravity vector with respect to a first data sample of the plurality of data samples using a determined orientation corresponding to the first data sample and a linear acceleration module configured to subtract the determined gravity vector from the first sample of data from the accelerometer to derive linear acceleration.

In an embodiment, the orientation module may apply a gain factor to convert accelerometer data to an angle or angular rate. As noted, the gain factor is based on a magnitude of acceleration. Further, the gain factor may be adjusted dynamically. As desired, the gain factor may be obtained from a look up table.

In one aspect, the orientation module may determine each orientation as the sum of previous orientation and a correction rotation comprising terms orthogonal to gravity applied to a previous orientation. For example, an orientation of the device corresponding to sample N of the plurality of samples may be represented by $\overline{Q_N}$ and may be determined as:

$$\overline{Q_N} = \overline{Q_{N-1}} + \begin{bmatrix} 0 \\ A_{wy} * \text{gain} \\ -A_{wx} * \text{gain} \\ 0 \end{bmatrix} \otimes \overline{Q_{N-1}},$$

wherein $A_{wy}$ is acceleration on a y-axis in a world frame, $A_{wx}$ is acceleration on an x-axis in the world frame and gain is a factor selected to convert accelerometer data to an angle or angular rate.

In an embodiment, the orientation module may determine the gravity vector with respect to the first data sample by converting a gravity vector in a world frame to a body frame of the device using the determined orientation corresponding to the first data sample.

In an embodiment, the linear acceleration module may high pass filter the derived linear acceleration.

The device may also include a magnetometer, such that the orientation module may determine the gravity vector by performing a sensor fusion operation with data from the magnetometer.

In an embodiment, the orientation module may determine the gravity vector by performing a sensor fusion operation with a previously derived linear acceleration.

DETAILED DESCRIPTION

Figure 1:
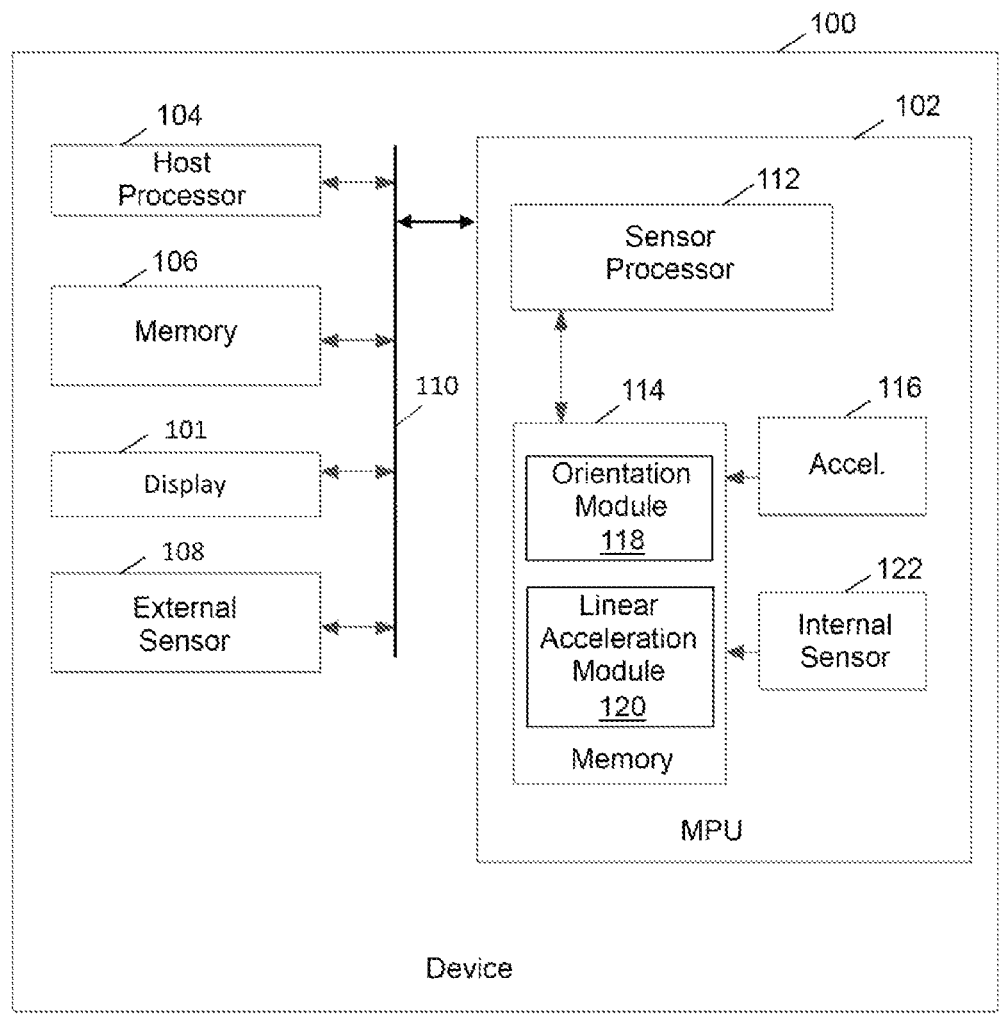
FIG. 1 is a schematic diagram of a device configured to measure linear acceleration using an accelerometer according to an embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings or chip embodiments. These and similar directional terms should not be construed to limit the scope of the disclosure in any manner.

In this specification and in the claims, it will be understood that when an element is referred to as being "connected to" or "coupled to" another element, it can be directly connected or coupled to the other element or intervening elements may be present. In contrast, when an element is referred to as being "directly connected to" or "directly coupled to" another element, there are no intervening elements present.

Some portions of the detailed descriptions which follow are presented in terms of procedures, logic blocks, processing and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "accessing," "receiving," "sending," "using," "selecting," "determining," "normalizing," "multiplying," "averaging," "monitoring," "comparing," "applying," "updating," "measuring," "deriving" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the exemplary wireless communications devices may include components other than those shown, including well-known components such as a processor, memory and the like.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the Internet or a local area network (LAN). Of course, many modifications may be made to this configuration without departing from the scope or spirit of the claimed subject matter.

The various illustrative logical blocks, modules, circuits and instructions described in connection with the embodiments disclosed herein may be executed by one or more processors, such as one or more motion processing units (MPUs), digital signal processors (DSPs), general purpose microprocessors, application specific integrated circuits (ASICs), application specific instruction set processors (ASIPs), field programmable gate arrays (FPGAs), or other equivalent integrated or discrete logic circuitry. The term "processor," as used herein may refer to any of the foregoing structure or any other structure suitable for implementation of the techniques described herein. In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an MPU and a microprocessor, a plurality of microprocessors, one or more microprocessors in conjunction with an MPU core, or any other such configuration.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

In the described embodiments, a chip is defined to include at least one substrate typically formed from a semiconductor material. A single chip may be formed from multiple substrates, where the substrates are mechanically bonded to preserve the functionality. A multiple chip includes at least two substrates, wherein the two substrates are electrically connected, but do not require mechanical bonding. A package provides electrical connection between the bond pads on the chip to a metal lead that can be soldered to a PCB. A package typically comprises a substrate and a cover. Integrated Circuit (IC) substrate may refer to a silicon substrate with electrical circuits, typically CMOS circuits. In some configurations, a substrate portion known as a MEMS cap provides mechanical support for the MEMS structure. The MEMS structural layer is attached to the MEMS cap. The MEMS cap is also referred to as handle substrate or handle wafer. In the described embodiments, an electronic device incorporating a sensor may employ a motion tracking module also referred to as Motion Processing Unit (MPU) that includes at least one sensor in addition to electronic circuits. The sensor, such as a gyroscope, a magnetometer, an accelerometer, a microphone, a pressure sensor, a proximity sensor, or an ambient light sensor, among others known in the art, are contemplated. Some embodiments include accelerometer, gyroscope, and magnetometer, which each provide a measurement along three axes that are orthogonal to each other. Such a device is often referred to as a 9-axis device. Other embodiments may not include all the sensors or may provide measurements along one or more axes. The sensors may be formed on a first substrate. Other embodiments may include solid-state sensors or any other type of sensors. The electronic circuits in the MPU receive measurement outputs from the one or more sensors. In some embodiments, the electronic circuits process the sensor data. The electronic circuits may be implemented on a second silicon substrate. In some embodiments, the first substrate may be vertically stacked, attached and electrically connected to the second substrate in a single semiconductor chip, while in other embodiments, the first substrate may be disposed laterally and electrically connected to the second substrate in a single semiconductor package.

In one embodiment, the first substrate is attached to the second substrate through wafer bonding, as described in commonly owned U.S. Pat. No. 7,104,129, which is incorporated herein by reference in its entirety, to simultaneously provide electrical connections and hermetically seal the MEMS devices. This fabrication technique advantageously enables technology that allows for the design and manufacture of high performance, multi-axis, inertial sensors in a very small and economical package. Integration at the wafer-level minimizes parasitic capacitances, allowing for improved signal-to-noise relative to a discrete solution. Such integration at the wafer-level also enables the incorporation of a rich feature set which minimizes the need for external amplification.

In the described embodiments, raw data refers to measurement outputs from the sensors which are not yet processed. Motion data may refer to processed and/or raw data. Processing may include applying a sensor fusion algorithm or applying any other algorithm. In the case of a sensor fusion algorithm, data from a plurality of sensors may be combined to provide, for example, an orientation of the device. In the described embodiments, a MPU may include processors, memory, control logic and sensors among structures.

As noted above, certain techniques of this disclosure are directed to measuring linear acceleration using data from an accelerometer alone. An accelerometer measures the linear acceleration imparted to the device by the movements of the user. In addition, the accelerometer also detects the acceleration due to gravity. Therefore, the raw data output by an accelerometer measures the combined acceleration both from the linear acceleration due to the movements of the device and the acceleration due to gravity. The accelerometer output may also include errors on in its measurement such as noise, an offset, a scaling error, and/or a cross axis error which may be mitigated using techniques known in the art. In many situations, accelerometer data is subjected to a sensor fusion operation with gyroscope and/or magnetometer data to estimate the orientation of the device. Although this may improve the orientation determination, the use of additional sensors may represent undesired power consumption. For example, providing gyroscope data may require significant energy expenditure.

In turn, the direction of gravity may as measured by the device be estimated and its magnitude assumed or otherwise determined. Correspondingly, linear acceleration may be computed by subtracting the gravity vector from the acceleration measurement as shown in Equation 1, where $[A_x, A_y, A_z]$ is the acceleration and $[G_x, G_y, G_z]$ is the gravity vector, both in the body frame of the device.

$$\overline{\text{Linear Accel}} = \begin{bmatrix} LA_x \\ LA_y \\ LA_z \end{bmatrix} = \begin{bmatrix} A_x - G_x \\ A_y - G_y \\ A_z - G_z \end{bmatrix} \quad (1)$$

As will be described below, the techniques of this disclosure provide an estimation of orientation of the device using accelerometer data alone. In turn, the gravity vector may be estimated and subtracted from the raw accelerometer data to provide a measurement of linear acceleration along the three orthogonal axes.

Details regarding one embodiment of a mobile electronic device 100 including features of this disclosure are depicted as high level schematic blocks in FIG. 1. As will be appreciated, device 100 may be implemented as a device or apparatus, such as a handheld device that can be moved in space by a user and its motion and/or orientation in space therefore sensed. For example, such a handheld device may be a mobile phone (e.g., cellular phone, a phone running on a local network, or any other telephone handset), wired telephone (e.g., a phone attached by a wire), personal digital assistant (PDA), video game player, video game controller, navigation device, activity or fitness tracker device (e.g., bracelet or clip), smart watch, other wearable device, mobile internet device (MID), personal navigation device (PND), digital still camera, digital video camera, binoculars, telephoto lens, portable music, video, or media player, remote control, or other handheld device, or a combination of one or more of these devices.

In some embodiments, device 100 may be a self-contained device that includes its own display 101 and other output devices in addition to input devices as described below. However, in other embodiments, device 100 may function in conjunction with another portable device or a non-portable device such as a desktop computer, electronic tabletop device, server computer, etc. which can communicate with the device 100, e.g., via network connections. The device may be capable of communicating via a wired connection using any type of wire-based communication protocol (e.g., serial transmissions, parallel transmissions, packet-based data communications), wireless connection (e.g., electromagnetic radiation, infrared radiation or other wireless technology), or a combination of one or more wired connections and one or more wireless connections.

As shown, device 100 includes MPU 102, host processor 104, host memory 106, and may include one or more sensors, such as external sensor 108. Host processor 104 may be configured to perform the various computations and operations involved with the general function of device 100. Host processor 104 may be coupled to MPU 102 through bus 110, which may be any suitable bus or interface, such as a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, or other equivalent. Host memory 106 may include programs, drivers or other data that utilize information provided by MPU 102. Exemplary details regarding suitable configurations of host processor 104 and MPU 102 may be found in co-pending, commonly owned U.S. patent application Ser. No. 12/106,921, filed Apr. 21, 2008, which is hereby incorporated by reference in its entirety.

In this embodiment, MPU 102 is shown to include sensor processor 112, memory 114 and accelerometer 116. Accelerometer may be implemented as a MEMS-based inertial sensor configured to provide raw data output corresponding to acceleration measured along three orthogonal axes or any equivalent structure. Memory 114 may store algorithms, routines or other instructions for processing data output by sensor 116, such as orientation module 118 and linear acceleration module 120 which are described in detail below. One or more additional internal sensors, such as internal sensor 122 may be integrated into MPU 102 as desired. If provided, external sensor 108 and/or internal sensor 122 may include one or more sensors, such as accelerometers, gyroscopes, magnetometers, pressure sensors, microphones, proximity, and ambient light sensors, and temperature sensors among others sensors. As used herein, an internal sensor refers to a sensor implemented using the MEMS techniques described above for integration with MPU 102 into a single chip. Similarly, an external sensor as used herein refers to a sensor carried on-board device 100 that is not integrated into MPU 102. In embodiments features an external sensor 108 and/or internal sensor 122, device 100 may be configured to perform conventional sensor fusion operations involving data from accelerometer 116. However, such capabilities may be considered as an adjunct to the techniques of this disclosure which utilize only accelerometer 116 data to measure linear acceleration. Further, even though embodiments are described in the context of accelerometer 116 integrated into MPU 102, these techniques may be applied to a non-integrated accelerometer, such as external sensor 108, which is local to device 100, or a remote sensor integrated into another device (e.g., bracelet, watch or other wearable), and the orientation and linear acceleration modules may be implemented using instructions stored in any available memory resource, such as host memory 106, that may be executed using any available processor, such as host processor 104. Still further, the functionality performed by the orientation and/or linear acceleration modules may be implemented using any combination of hardware, firmware and software.

As will be appreciated, host processor 104 and/or sensor processor 112 may be one or more microprocessors, central processing units (CPUs), or other processors which run software programs for device 100 or for other applications related to the functionality of device 100. For example, different software application programs such as menu navigation software, games, camera function control, navigation software, and phone or a wide variety of other software and functional interfaces can be provided. In some embodiments, multiple different applications can be provided on a single device 100, and in some of those embodiments, multiple applications can run simultaneously on the device 100. Multiple layers of software can be provided on a computer readable medium such as electronic memory or other storage medium such as hard disk, optical disk, flash drive, etc., for use with host processor 104 and sensor processor 112. For example, an operating system layer can be provided for device 100 to control and manage system resources in real time, enable functions of application software and other layers, and interface application programs with other software and functions of device 100. In some embodiments, one or more motion algorithm layers may provide motion algorithms for lower-level processing of raw sensor data provided from internal or external sensors. Further, a sensor device driver layer may provide a software interface to the hardware sensors of device 100. Some or all of these layers can be provided in host memory 106 for access by host processor 104, in memory 114 for access by sensor processor 112, or in any other suitable architecture. In some embodiments, it will be recognized that the exemplary architecture depicted in FIG. 1 may allow the measurement of linear acceleration including the processing of data from accelerometer 116 to be performed using MPU 102 and may not require involvement of host processor 104 and/or host memory 106. The host processor 104 may be in a power save ("sleep') mode, and the MPU 102 may wake up the host processor 104 once the linear acceleration has been determined. Likewise, since the techniques require only data from accelerometer 116, linear acceleration may be measured without utilizing data from external sensor 108 or additional internal sensor 122, if provided. Thus, such additional sensors may be omitted or may be operated in a power save ("sleep") mode. Correspondingly, the techniques of this disclosure allow for measurement of linear acceleration of device 100 in a power and computationally efficient manner.

Figure 2:
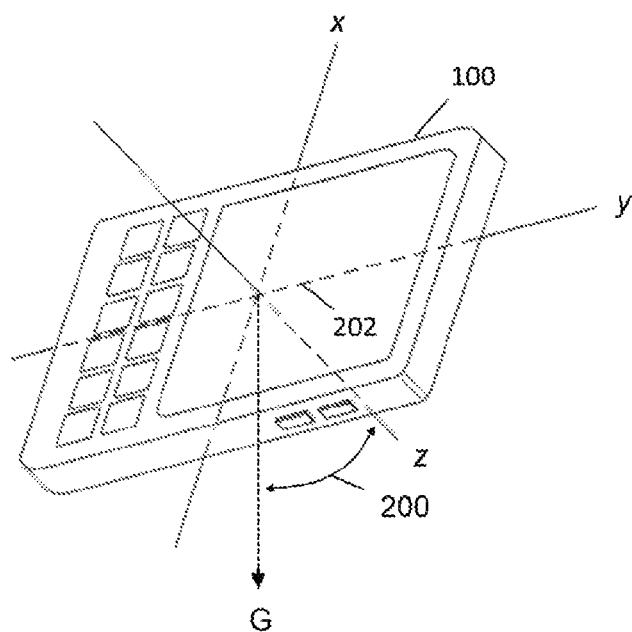
FIG. 2 is a schematic diagram of the orientation of a device with respect to gravity according to an embodiment.

As described herein, the body frame 202 may have three orthogonal axes fixed to device 100 as depicted in FIG. 2. Switching from the body frame to the world frame or vice versa may be performed by apply the appropriate rotation to the data. Similarly, the world frame may have axes fixed to the Earth, such as by aligning the Z axis of the world frame with the gravity vector resulting from Earth's gravity field, pointing from the surface of the Earth to the sky. Although the math and descriptions provided in this disclosure are in the context of these frames, one of skill in the art will realize that similar operations may be performed using other definitions and frames of reference. All the teachings could be redone with different definitions.

In one aspect, the orientation of device 100 may be expressed as the rotational operation that translates the body frame 202 to the world frame. For example, the orientation of device 100 as depicted in FIG. 2 may be rotation operation 200 that would align the Z axis of the body frame with the gravity vector. In some embodiments, rotation operation 200 may be expressed in the form of a unit quaternion. As used herein, the terms "quaternion" and "unit quaternion" may used interchangeably for convenience. Accordingly, a quaternion may be a four element vector describing the transition from one rotational orientation to another rotational orientation and may be used to represent the orientation of device 100. A unit quaternion has a scalar term and 3 imaginary terms. In this disclosure, the quaternion is expressed with the scalar term first followed by the imaginary terms but, appropriate modifications may be made to the formulas, equations and operations to accommodate different definitions of quaternion. Thus, rotation operation 200 representing the orientation of device 100 may be described as a rotation of angle θ about the unit vector $[u_x, u_y, u_z]$ as indicated by Equation 2.

$$\overline{Q} = \begin{bmatrix} \cos\left(\frac{\theta}{2}\right) \\ \sin\left(\frac{\theta}{2}\right) \cdot u_x \\ \sin\left(\frac{\theta}{2}\right) \cdot u_y \\ \sin\left(\frac{\theta}{2}\right) \cdot u_z \end{bmatrix} \quad (2)$$

In other embodiments, rotation operation 200 may be expressed in any other suitable manner. For example, a rotation matrix or Euler angles may be used to represent sequential rotations with respect to fixed orthogonal axes, such as e.g. rotations in the yaw, pitch and roll directions. As such, the operations described below may be modified as appropriate to utilize rotation matrices if desired.

Raw data output by accelerometer 116 may be in the form of an acceleration component for each orthogonal axis of the body frame, such as $A_x$, $A_y$ and $A_z$. Conversion of this data to acceleration in the world frame, $A_{wx}$, $A_{wy}$, and $A_{wz}$ may be performed readily using quaternion multiplication and inversion. For quaternions $$\overline{Q_1} = \begin{bmatrix} q_{1w} \\ q_{1x} \\ q_{1y} \\ q_{1z} \end{bmatrix}$$

and $$\overline{Q_2} = \begin{bmatrix} q_{2w} \\ q_{2x} \\ q_{2y} \\ q_{2z} \end{bmatrix},$$

quaternion multiplication may be designated using the symbol "⊗" and defined as shown in Equation 3 while quaternion inversion may be designated using the symbol "'" and defined as shown in Equation 4.

$$\overline{Q_1} \otimes \overline{Q_2} = \begin{bmatrix} q_{1w} \cdot q_{2w} - q_{1x} \cdot q_{2x} - q_{1y} \cdot q_{2y} - q_{1z} \cdot q_{2z} \\ q_{1w} \cdot q_{2x} + q_{1x} \cdot q_{2w} + q_{1y} \cdot q_{2z} - q_{1z} \cdot q_{2x} \\ q_{1w} \cdot q_{2y} - q_{1x} \cdot q_{2z} + q_{1y} \cdot q_{2w} + q_{1z} \cdot q_{2x} \\ q_{1w} \cdot q_{2z} + q_{1x} \cdot q_{2y} - q_{1y} \cdot q_{2x} + q_{1z} \cdot q_{2w} \end{bmatrix} \quad (3)$$

$$\overline{Q'_1} = \begin{bmatrix} q_{1w} \\ -q_{1x} \\ -q_{1y} \\ -q_{1z} \end{bmatrix} \quad (4)$$

The acceleration in the world frame may be converted to the acceleration in the body frame using a known orientation. Equation 5 shows the quaternion multiplication of the orientation $Q_{N-1}$ with the acceleration in the body frame to calculate the acceleration in the world frame:

$$\overline{Q_{Aw}} = \begin{bmatrix} 0 \\ Awx \\ Awy \\ Awz \end{bmatrix} = \overline{Q_{N-1}} \otimes \begin{bmatrix} 0 \\ Ax \\ Ay \\ Az \end{bmatrix} \otimes \overline{Q'_{N-1}}$$

When the device is not moving, the orientation is constant and there is no linear acceleration. If there is no error on the acceleration measurements, the accelerometer only measures the acceleration in the body frame due to gravity. Assuming that there is no error on the quaternion, this means that $A_{wx}$ and $A_{wy}$ are zero and $A_{wz}$ equals the gravitational acceleration, i.e. the acceleration vector in the world frame is identical to the gravitational vector.

On the other hand, if the device is moving, the accelerometers also measures the linear acceleration. After the conversion to the world frame using Equation 5, the accelerations $A_{wx}$ and $A_{wy}$ are not zero and the acceleration vector in the world frame has a different orientation than gravity. In a similar manner, Equation 5 shows that any error on the orientation, i.e. any error on the quaternion $Q_{N-1}$ will also lead to $A_{wx}$ and $A_{wy}$ not being zero and an error on the acceleration vector in the world frame.

The fact that an error in the determined orientation $Q_{N-1}$ leads to a non-zero $A_{wx}$ and $A_{wy}$ can be used in a correction filter to calculate the correct orientation in combination with the concept that a quaternion with an error in orientation needs a rotation to correct it. Equation 6 shows how this correction can be performed using the $A_{wx}$ and $A_{wy}$ as determined by equation 5:

$$\overline{Q_N} = \overline{Q_{N-1}} + \begin{bmatrix} 0 \\ A_{wy} * \text{gain} \\ -A_{wx} * \text{gain} \\ 0 \end{bmatrix} \otimes \overline{Q_{N-1}} \quad (6)$$

In one aspect, $\overline{Q_N}$ may be scaled to unity, such as by using Equation 7.

$$\overline{Q_N} = \frac{\overline{Q_N}}{\|\overline{Q_N}\|} \quad (7)$$

The gain term may be configured to scale the acceleration and convert the measurement unit output of the acceleration to an angle, as the correction quaternion needs to be expressed in angles.

As a practical matter, the typical motion of the device 100 imparted by the user does not create a constant acceleration. Accordingly, over a period of time, the majority of acceleration measured by accelerometer 116 may be attributed to gravity. Therefore, the quaternion $Q_N$ as determined by equation 6 can be used as a new input to equation 5, thus creating an iterative filter. Over time, this filter removes the linear acceleration contribution, and the quaternion $Q_N$ will converge to the correct orientation as the error on the quaternion decreases and the accelerations $A_{wx}$ and $A_{wy}$ approach zero.

The thus determined orientation $Q_N$ can be used to determine the gravity in the body frame using a similar, but inversed, approach as in equation 5. By selecting units that allow the magnitude of the gravity vector to be expressed as 1 unit=9.80665 m/s² and given an orientation of device 100 at the time sample N of accelerometer data is output expressed as $\overline{Q_N}$, the world frame gravity vector $[0,0,1]^T$ may be converted to the gravity vector G in the body frame $[G_x, G_y, G_z]^T$ using Equation 8:

$$\overline{G} = \begin{bmatrix} 0 \\ G_x \\ G_y \\ G_z \end{bmatrix} = \overline{Q'_N} \otimes \begin{bmatrix} 0 \\ 0 \\ 0 \\ 1 \end{bmatrix} \otimes \overline{Q_N} \quad (8)$$

In some embodiments, rather than assuming a magnitude of the gravity vector as being one to represent the force of gravity at sea level, the magnitude of gravity may be adjusted using a geographic position of device 100, such as may be obtained using global positioning satellite (GPS) data, signal ranging techniques, user input, or any other suitable methods.

Once suitable convergence in $\overline{Q_N}$ has been achieved, such as may occur given sufficient iterations of processing samples of data from accelerometer 116 as discussed above in relation to the filtering, orientation module 118 may output an orientation of device 100 determined using only data from accelerometer 116. Although this orientation may not provide a heading for device 100, the gravity vector also lacks a heading term. Accordingly, orientation module 118 may use the orientation represented by $\overline{Q_N}$ to determine a gravity vector in the body frame corresponding to sample N, such as by applying Equation 8. Linear acceleration module 120 may then be employed to subtract the determined gravity vector from data sample N from accelerometer 116. In one aspect, linear acceleration module 120 may be configured to use Equation 1 and subtract the gravity vector as determined by Equation 8, resulting in Equation 9.

$$\overline{\text{Linear Accel}} = \begin{bmatrix} LA_x \\ LA_y \\ LA_z \end{bmatrix} = \begin{bmatrix} A_x - 2 \cdot Q_x \cdot Q_z + 2 \cdot Q_w \cdot Q_y \\ A_y - 2 \cdot Q_w \cdot Q_x - 2 \cdot Q_y \cdot Q_z \\ A_z + 2 \cdot Q_x \cdot Q_x + 2 \cdot Q_y \cdot Q_y - 1 \end{bmatrix} \quad (9)$$

Depending on the application or intended use of the data, linear acceleration may be output in the body frame, such as indicated by Equation 9, or may be converted to the world frame, such as through the use of Equation 5 or the equivalent, or both.

The gain as introduced in equation 6 determines to what extend the calculated accelerations $A_{wx}$ and $A_{wy}$ from equation 5 are used to correct the orientation $Q_{N-1}$. Therefore, theses accelerations control the amplitude of the iteration steps. As desired, gain may represent a constant or may be dynamically determined based at least in part on a factor such as the magnitude of the measured acceleration or a power of the magnitude to provide the appropriate scaling of the accelerometer data. For example, for large acceleration values, a smaller gain may be chosen to avoid too large iteration steps. In one embodiment, the values for gain may be stored in a look up table. In another embodiment, the values may be determined using an appropriate algorithm.

In another embodiment, one of skill in the art will recognize that a more precise estimation of angles that may be used to rotate the quaternion to drive $A_{wx}$ and $A_{wy}$ towards zero may be calculated. In turn, the estimated angles, or a fraction of the angles representing an appropriate filtering function, may be used in a quaternion update operation corresponding to Equation 6. Such an embodiment may be configured to achieve a convergence to a $\overline{Q_N}$ representing orientation of device 100 in fewer iterations, but may require increased computational resources.

As desired, a residual term in estimating linear acceleration that remains due to a bias in accelerometer 116 may be removed by high pass filtering the determined linear acceleration. Since linear acceleration should approach zero over time as discussed above, an appropriate high pass filter may be used to identify an offset corresponding to bias in accelerometer 116 as known to those of skill in the art.

In one aspect, device 100 may include a magnetometer in the form of external sensor 108 or additional internal sensor 122. Magnetometer data may be supplied to orientation module 118 for use in a sensor fusion operation to enhance determination of the orientation of the device and the gravity vector.

Figure 3:
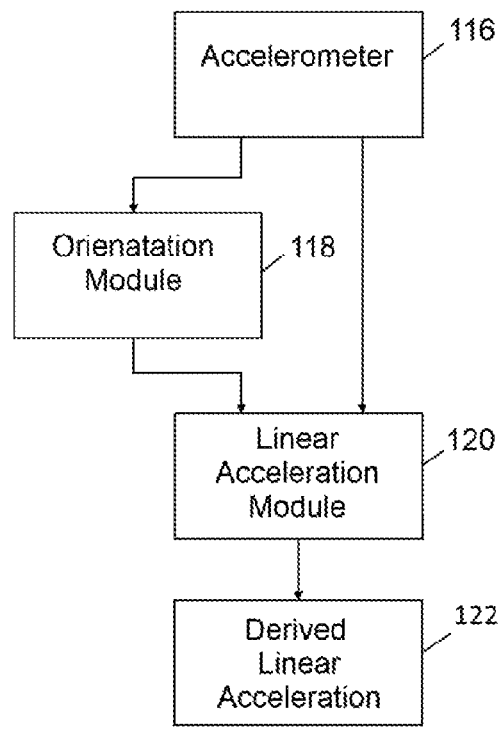
FIG. 3 is a schematic diagram of accelerometer data flow according to an embodiment.
Figure 4:
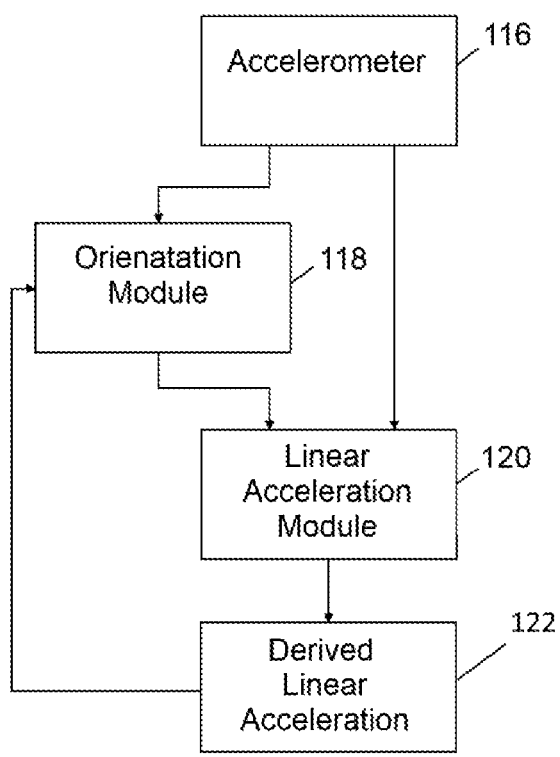
FIG. 4 is a schematic diagram of accelerometer data flow according to another embodiment.

One suitable flow of data provided by accelerometer 116 is depicted schematically in FIG. 3. As shown, data from accelerometer 116 is output both to orientation module 118 and to linear acceleration module 120. Using the operations described above, or a suitable equivalent, orientation module 118 provides linear acceleration module 120 with determined orientations of device 100 for a current sample of data. Correspondingly, linear acceleration module 120 may use the determined orientation associated with a given sample of data to subtract a gravity vector and provide a measured linear acceleration, indicated as derived linear acceleration 122. In a further aspect schematically depicted in FIG. 4, the measured linear acceleration, indicated as derived linear acceleration 122, output by linear acceleration module 120 may be fed back to orientation module 118 to for use in a sensor fusion operation to enhance determination of the gravity vector. For example, to adjust the gain depending on the determined linear acceleration.

Figure 5:
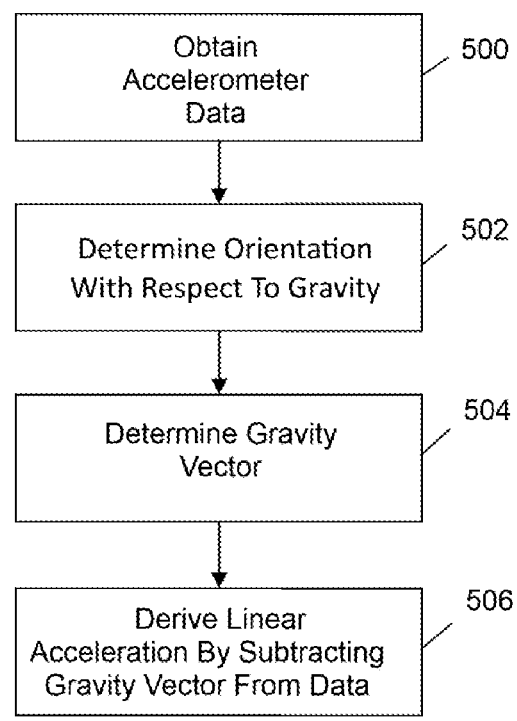
FIG. 5 is flowchart showing a routine for measuring linear acceleration using only accelerometer data according to an embodiment.

To help illustrate aspects of this disclosure, an exemplary routine for measuring linear acceleration of device 100 using only accelerometer data is represented by the flowchart shown in FIG. 5. Beginning with 500, a plurality of data samples may be obtained from an accelerometer, such as accelerometer 116. In 502, orientation module 118 may determine a plurality of orientations of device 100 with respect to gravity. As described above, each orientation may correspond to one of the plurality of data samples and may be iteratively derived from a previous determined orientation. Next, in 504, linear acceleration module 120 may determine a gravity vector corresponding to one of the data samples using a determined orientation. Linear acceleration module 120 may then subtract the gravity vector from the data sample to provide a measured linear acceleration as indicated by 506.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the present invention.

What is claimed is:

1. A method for measuring linear acceleration for a device having an accelerometer comprising:
   obtaining a plurality of data samples from the accelerometer;
   iteratively determining a plurality of orientations of the device with respect to gravity using only sampled data from the accelerometer;
   determining a gravity vector with respect to a first data sample of the plurality of data samples using a determined orientation corresponding to the first data sample; and
   subtracting the determined gravity vector from the first sample of data from the accelerometer to derive linear acceleration.

2. The method of claim 1, further comprising applying a gain factor to the plurality of data samples to convert accelerometer data to an angle.

3. The method of claim 2, wherein the gain factor is based on a magnitude of acceleration.

4. The method of claim 2, wherein the gain factor is adjusted dynamically.

5. The method of claim 2, wherein the gain factor is obtained from a look up table.

6. The method of claim 1, wherein each orientation is determined as the sum of previous orientation and a correction rotation comprising terms orthogonal to gravity applied to a previous orientation.

7. The method of claim 6, wherein an orientation of the device corresponding to sample N of the plurality of samples is represented by $Q_N$ and is determined as:

$$\overline{Q}_N = \overline{Q}_{N-1} + \begin{bmatrix} 0 \\ A_{wy} * \text{gain} \\ -A_{wx} * \text{gain} \\ 0 \end{bmatrix} \otimes \overline{Q}_{N-1},$$

wherein $A_{wy}$ is acceleration on a y-axis in a world frame, $A_{wx}$ is acceleration on an x-axis in the world frame and gain is a factor selected to convert accelerometer data to an angle.

8. The method of claim 1, wherein determining the gravity vector with respect to the first data sample comprises converting a gravity vector in a world frame to a body frame of the device using the determined orientation corresponding to the first data sample.

9. The method of claim 1, further comprising high pass filtering the derived linear acceleration.

10. The method of claim 1, wherein determining the gravity vector further comprises performing a sensor fusion operation with data from a magnetometer of the device.

11. The method of claim 1, wherein determining the gravity vector of the device comprises performing a sensor fusion operation with a previously derived linear acceleration.

12. A device for measuring linear acceleration comprising:
- an accelerometer outputting a plurality of data samples;
- an orientation module configured to iteratively determine a plurality of orientations of the device with respect to gravity using only sampled data from the accelerometer and to determine a gravity vector with respect to a first data sample of the plurality of data samples using a determined orientation corresponding to the first data sample; and
- a linear acceleration module configured to subtract the determined gravity vector from the first sample of data from the accelerometer to derive linear acceleration.

13. The device of claim 12, wherein the orientation module is configured to apply a gain factor to the plurality of data samples to convert accelerometer data to an angle.

14. The device of claim 13, wherein the gain factor is based on a magnitude of acceleration.

15. The device of claim 13, wherein the orientation module is configured to adjust the gain factor dynamically.

16. The device of claim 13, wherein the orientation module is configured to obtain the gain factor from a look up table.

17. The device of claim 12, wherein the orientation module is configured to determine each orientation as the sum of previous orientation and a correction rotation comprising terms orthogonal to gravity applied to a previous orientation.

18. The device of claim 17, wherein an orientation of the device corresponding to sample N of the plurality of samples is represented by $Q_N$ and is determined as:
wherein $A_{wy}$ is acceleration on a y-axis in a world frame, $A_{wx}$ is acceleration on an x-axis in the world frame and gain is a factor selected to convert accelerometer data to an angle.

19. The device of claim 12, wherein the orientation module is configured to determine the gravity vector with respect to the first data sample by converting a gravity vector in a world frame to a body frame of the device using the determined orientation corresponding to the first data sample.

20. The device of claim 12, wherein the linear acceleration module is configured to high pass filter the derived linear acceleration.

21. The device of claim 12, further comprising a magnetometer, wherein the orientation module is configured to perform a sensor fusion operation with data from the magnetometer.

22. The device of claim 12, wherein the orientation module is configured to determine the gravity vector by performing a sensor fusion operation with a previously derived linear acceleration.

* * * * *